United States Patent
Endoh (10) Patent No.: US 9,819,851 B2
(45) Date of Patent: Nov. 14, 2017

(54) IMAGING SYSTEM, CONTROL APPARATUS, AND CONTROL METHOD THEREOF

(71) Applicant: CANON KABUSHIKI KAISHA, Tokyo (JP)

(72) Inventor: Kenta Endoh, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 15/077,044

(22) Filed: Mar. 22, 2016

(65) Prior Publication Data

US 2016/0295094 A1 Oct. 6, 2016

(30) Foreign Application Priority Data

Mar. 31, 2015 (JP) ................................. 2015-073214

(51) Int. Cl.
*H01L 27/146* (2006.01)
*H04N 5/232* (2006.01)
*H04N 5/32* (2006.01)

(52) U.S. Cl.
CPC .......... *H04N 5/23206* (2013.01); *H04N 5/32* (2013.01)

(58) Field of Classification Search
CPC .. H05G 1/08; H04N 5/23206; H04N 5/23293; G03B 42/04; G05F 19/321
See application file for complete search history.

(56) References Cited

U.S. PATENT DOCUMENTS

| | | | | |
|---|---|---|---|---|
| 2011/0075811 A1* | 3/2011 | Enomoto | ................. | A61B 6/00 378/98.5 |
| 2013/0102245 A1* | 4/2013 | Ohguri | ................... | A61B 6/548 455/39 |
| 2013/0279657 A1* | 10/2013 | Hiroike | ................... | H05G 1/08 378/62 |
| 2015/0201899 A1* | 7/2015 | Uchinomiya | ........ | A61B 6/4405 378/62 |

FOREIGN PATENT DOCUMENTS

JP 2010-268822 12/2010 ............... A61B 6/00

* cited by examiner

*Primary Examiner* — Kiho Kim
(74) *Attorney, Agent, or Firm* — Fitzpatrick, Cella, Harper & Scinto

(57) ABSTRACT

An imaging system includes at least one image capturing apparatus and a control apparatus that selectively performs wireless connection with the at least one image capturing apparatus. The control apparatus includes a wireless station communication unit configured to operate as a wireless station device, a storage unit configured to store, in association with a predetermined imaging condition, connection setting information for wirelessly connecting with the at least one image capturing apparatus, and a connection control unit configured to set, if an imaging condition designated by a user matches with the predetermined imaging condition, the connection setting information associated with the predetermined imaging condition in the wireless station communication unit and perform control so as to wirelessly connect with the at least one image capturing apparatus.

10 Claims, 7 Drawing Sheets

IMAGING SYSTEM, CONTROL APPARATUS, AND CONTROL METHOD THEREOF

BACKGROUND OF THE INVENTION

Field of the Invention

The present invention relates to a technique of controlling imaging via wireless communication.

Description of the Related Art

In recent years, an X-ray imaging system is used in various fields. Particularly, it has become one of the important means for diagnosis in the medical field. In an X-ray imaging system of the medical field, X-rays generated from an X-ray generation unit irradiate an object via an X-ray irradiation unit, and the X-rays transmitted through the object are obtained as an X-ray image by the X-ray imaging apparatus. The X-ray imaging apparatus transmits the obtained X-ray image to, for example, a control apparatus, and the control apparatus performs image processing on the X-ray image and displays the image on a monitor.

In a case in which the X-ray imaging system is arranged as a visiting car (a mobile X-ray apparatus), wireless communication is preferred as the method to connect the units as it facilitates installation and operation. For example, as exemplified in FIG. 9A, the system generally has a three-unit arrangement in which a wireless communication access point device is installed in the visiting car and the X-ray imaging apparatus and the control apparatus formed as station devices are connected via the access point device of the visiting car. In this arrangement, an X-ray image obtained by X-ray irradiation is wirelessly transmitted from the X-ray imaging apparatus to the control apparatus via the access point and is displayed on a display device after image processing or the like is performed in the control apparatus.

Figure 9A:
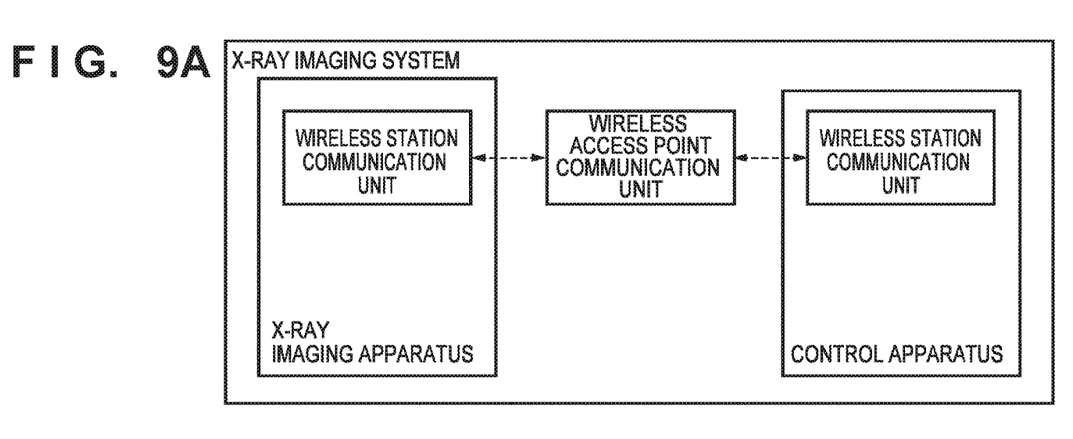
FIGS. 9A and 9B are views showing examples of the arrangement of an X-ray imaging system.
Figure 9B:
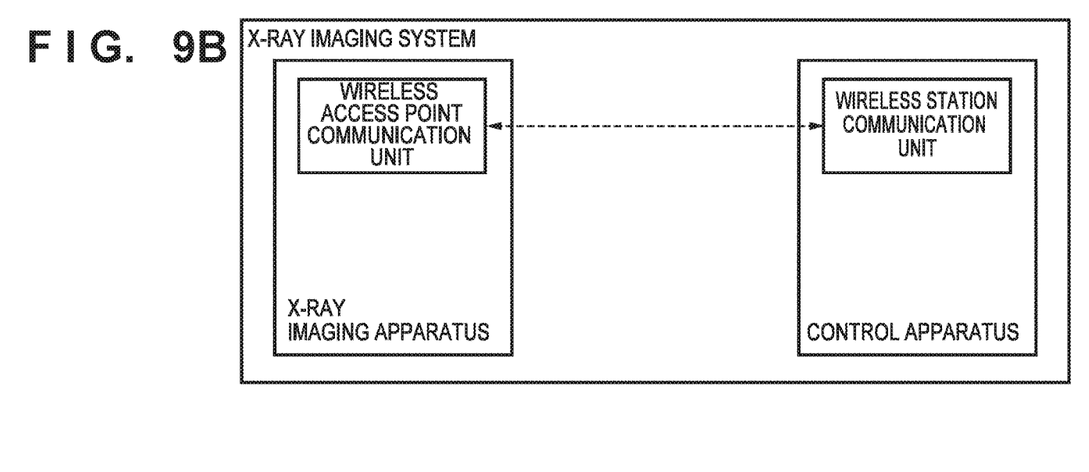

In addition, by incorporating the function of the access point device into an X-ray imaging apparatus, a two-unit arrangement as that shown in FIG. 9B becomes possible, and the portability can be improved.

Furthermore, Japanese Patent Laid-Open No. 2010-268822 discloses a technique that supports the correction of an imaging condition such as the exposure amount of radiation and imaging order information such as the selection of the imaging portion to be used, the imaging part and the name, the height and weight of the patient, and the like.

In the three-unit arrangement shown in FIG. 9A, the control apparatus can connect with a plurality of X-ray imaging apparatuses which are connected to the same access point device and use the X-ray imaging apparatuses for imaging. Therefore, the control apparatus can switch the X-ray imaging apparatus to be used for imaging without having to perform switching of wireless connection.

However, in the two-unit arrangement shown in FIG. 9B, the control apparatus is required to selectively connect with an X-ray imaging apparatus and cannot connect with a plurality of X-ray imaging apparatuses at once. Therefore, in a case in which each of the plurality of X-ray imaging apparatuses is to be used according to the situation, it becomes necessary for the control apparatus to appropriately switch the wireless connection to the X-ray imaging apparatus to be used.

SUMMARY OF THE INVENTION

According to one aspect of the present invention, an imaging system comprises at least one image capturing apparatus and a control apparatus that selectively performs wireless connection with one of the at least one image capturing apparatus, wherein each of the at least one image capturing apparatus comprises a wireless access point communication unit configured to operate as a unique wireless access point device, and the control apparatus comprises: a wireless station communication unit configured to operate as a wireless station device, a storage unit configured to store, in association with a predetermined imaging condition, connection setting information for wirelessly connecting with one of the at least one image capturing apparatus, and a connection control unit configured to set, if an imaging condition designated by a user matches with the predetermined imaging condition, the connection setting information associated with the predetermined imaging condition in the wireless station communication unit and perform control so as to wirelessly connect with one of the at least one image capturing apparatus.

According to another aspect of the present invention, an imaging system comprises a first image capturing apparatus, a second image capturing apparatus, and a control apparatus configured to selectively connect with one of the first and second image capturing apparatuses, wherein the first image capturing apparatus comprises: a first wireless access point communication unit configured to operate as a first wireless access point device, the second image capturing apparatus comprises: a second wireless access point communication unit configured to operate as a second wireless access point device and a first wired communication unit configured to perform wired communication with the control apparatus, the control apparatus comprises: a wireless station communication unit configured to operate as a wireless station device, a second wired communication unit configured to perform wired communication with the second image capturing apparatus, a storage unit configured to store, in association with a predetermined imaging condition, connection setting information for connecting to one of the first image capturing apparatus and the second image capturing apparatus, and a connection control unit configured to set, if an imaging condition designated by a user matches with the predetermined imaging condition, the connection setting information associated with the predetermined imaging condition in the wireless station communication unit and performs control so as to connect with one of the first and second image capturing apparatuses, and if connecting to the second image capturing apparatus, the connection control unit connects by wired connection if wired connection via the second wired communication unit is possible and connects by wireless communication via the wireless station communication unit if the wired connection via the second wired communication unit is impossible.

According to still another aspect of the present invention, a control apparatus that selectively and wirelessly connects with one of at least one image capturing apparatus operating as a unique wireless access point device, comprises: a wireless station communication unit configured to operate as a wireless station device, a storage unit configured to store, in association with a predetermined imaging condition, connection setting information for wirelessly connecting with one of the at least one image capturing apparatus, and a connection control unit configured to set, if an imaging condition designated by a user matches with the predetermined imaging condition, the connection setting information associated with the predetermined imaging condition in the wireless station communication unit and perform control so as to wirelessly connect with one of the at least one image capturing apparatus.

According to yet another aspect of the present invention, a control method of a control apparatus that selectively and wirelessly connects with one of at least one image capturing apparatus operating as a unique wireless access point device, wherein the control apparatus comprises a storage unit configured to store, in association with a predetermined imaging condition, connection setting information for wirelessly connecting with one of the at least one image capturing apparatus, and the control method comprises: accepting designation of an imaging condition from a user, and performing connection control so as to wirelessly connect to one of the at least one image capturing apparatus by using the connection setting information associated with the predetermined imaging condition if the imaging condition accepted in the accepting matches the predetermined imaging condition.

The present invention improves the portability of the entire imaging system and allows more than one imaging apparatus to be suitably used.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Preferred embodiments of the present invention will be described in detail below with reference to the accompanying drawings. Note that the following embodiments are merely examples and are not intended to limit the scope of the present invention.

First Embodiment

The first embodiment of an imaging system according to the present invention will be described below by taking an X-ray imaging system using a wireless LAN as an example.

<System Arrangement>

Figure 1:
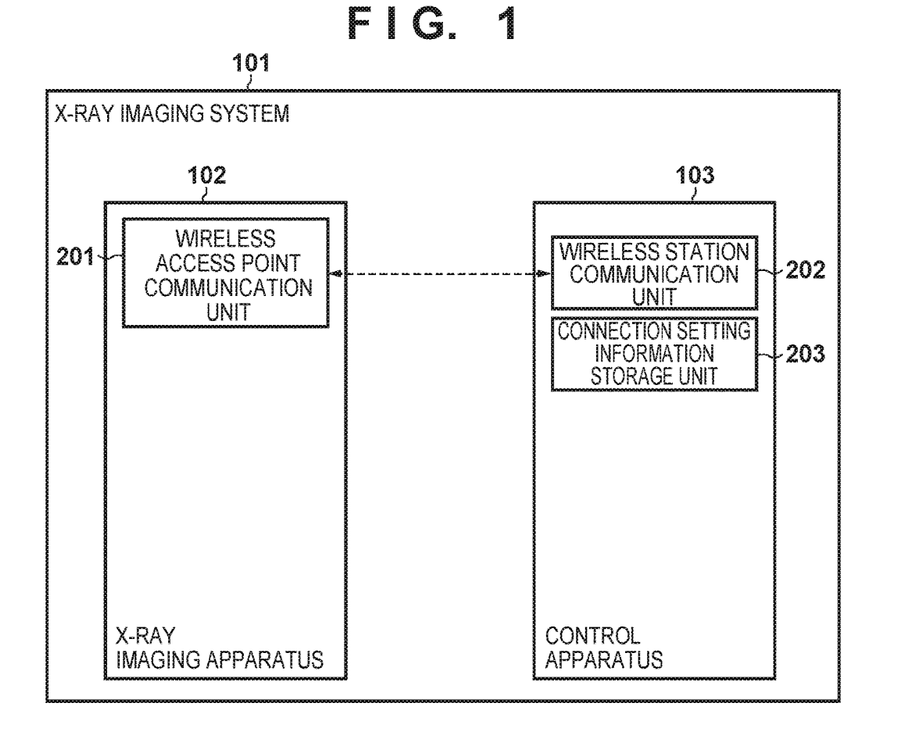
FIG. 1 is a view showing the arrangement of an X-ray imaging system according to the first embodiment.

FIG. 1 is a view showing the arrangement of an X-ray imaging system according to the first embodiment. The X-ray imaging system is, for example, installed in a visiting car (a mobile X-ray apparatus). An X-ray imaging system 101 is formed from two units, an X-ray imaging apparatus 102 and a control apparatus 103, in the same manner as the arrangement of FIG. 9B. Note that the X-ray imaging system can be formed to further include units that are not shown. In addition, although only functional units related to the control of wireless communication are shown in FIG. 1, other functional units are provided in practice. Furthermore, although only one X-ray imaging apparatus 102 is shown in FIG. 1, two or more X-ray imaging apparatuses can be present.

For example, the X-ray imaging apparatus 102 includes an X-ray generation unit for generating X-rays, an X-ray irradiation unit for irradiating a predetermined range with X-rays, and an imaging unit for receiving the X-rays and generating an X-ray image. Assume that a flat panel detector (FPD) is used as the imaging unit. Detection elements (pixels) are arranged in a matrix on the detector surface of the FPD. The FPD accumulates signal charges generated for each pixel in accordance with the radiation detection amount and obtains corresponding digital data after A/D converting the signal charges.

The control apparatus 103 is formed to control not only the connection control of wireless connection with the X-ray imaging apparatus 102 but also the operation of each unit (the above-described X-ray generation unit, X-ray irradiation unit, and imaging unit) of the X-ray imaging apparatus 102. In addition, the control apparatus 103 includes an image processing unit for image processing of the X-ray image obtained from the X-ray imaging apparatus 102 and a monitor for displaying the X-ray image that has undergone image processing.

The X-ray imaging apparatus 102 irradiates an object (a specific part of the human body) via an X-ray irradiation unit with X-rays generated from the X-ray generation unit and obtains, by the imaging unit, the X-rays transmitted through the object as an X-ray image. The X-ray imaging apparatus 102 then transmits the obtained X-ray image to the control apparatus 103. The control apparatus 103 performs image processing and the like on the X-ray image and displays the processed X-ray image on the monitor.

As described above, the X-ray imaging system according to the first embodiment is formed so that the X-ray imaging apparatus 102 operates as a wireless access point device and the control apparatus 103 operates as a wireless station device in the same manner as those in the arrangement of FIG. 9B. More specifically, the X-ray imaging apparatus 102 includes a wireless access point communication unit 201 which operates as a wireless LAN access point (AP). On the other hand, the control apparatus 103 includes a wireless station communication unit 202 which operates as a wireless LAN station (STA). The wireless station communication unit 202 is configured to be capable of selectively and wirelessly connecting with one or more X-ray imaging apparatuses 102. In the first embodiment, the control apparatus 103 further includes a connection setting information storage unit 203 that stores information used for automatic connection operation of wireless connection. The information stored in the connection setting information storage unit 203 will be further described below.

Figure 2:
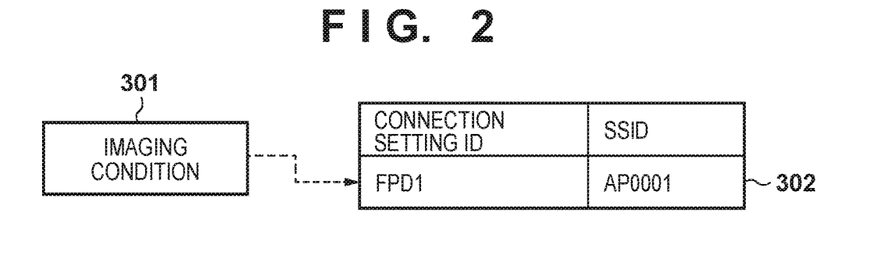
FIG. 2 is a view for explaining association of an imaging condition and connection setting information.

FIG. 2 is a view for explaining association between an imaging condition and the connection setting information stored in the connection setting information storage unit 203.

An imaging condition 301 includes necessary information to perform one imaging. Assume that information of a body part to be imaged (such as "lung") is included as the imaging condition.

In contrast, connection setting information 302 includes information for connecting with an access point. In this case, assume that the information includes an "SSID" which is the network identification name of the wireless LAN and a "connection setting ID" which is the connection setting index. The connection setting information 302 is associated in advance with a corresponding imaging condition 301 and stored in the connection setting information storage unit 203. For example, a specific access point (wireless access point communication unit 201) is associated in advance with a specific body part to be imaged.

Note that, although information of a body part to be imaged was shown as the imaging condition 301 in this example, the imaging condition 301 can be formed to include other kinds of information (for example, information indicating the unique apparatus identifier of the X-ray imaging apparatus, the type of the X-ray imaging apparatus, the exposure amount of radiation or the imaging direction). In addition, although an "SSID" is shown as the connection setting information 302, the connection setting information 302 can be formed to further include other kinds of information (information about encryption and authentication or the like). Note that although only one pair of information consisting of one imaging condition 301 and one connection setting information 302 are shown in FIG. 2, the connection setting information storage unit 203 can be formed to store a plurality of pairs of information.

<System Operation>

The connection operation between the wireless access point communication unit 201 of the X-ray imaging apparatus 102 and the wireless station communication unit 202 of the control apparatus 103 will be described below. In the initial state, assume that the connection between the wireless access point communication unit 201 and the wireless station communication unit 202 has not been established.

The control apparatus 103 accepts an instruction to start X-ray imaging from a user (radiographer or the like) via an operation unit (not shown). For example, the control apparatus 103 accepts designation of the body part to be imaged, that is, designation of the imaging condition 301 via the operation unit.

Upon accepting the designation of the imaging condition 301, the control apparatus 103 selects the connection setting information 302 associated with the imaging condition 301. Then, the control apparatus 103 sets the selected connection setting information 302 in the wireless station communication unit 202.

Based on the set connection setting information 302, the wireless station communication unit 202 connects to a specific access point (the wireless access point communication unit 201 in this embodiment) corresponding to the connection setting information 302. Subsequently, the control apparatus 103 executes X-ray imaging by controlling the X-ray imaging apparatus 102 via the established wireless connection.

According to the above-described first embodiment, the operator need only select the imaging condition to establish wireless connection with the X-ray imaging apparatus 102 that is appropriate for the imaging. That is, the operator need not consider which X-ray imaging apparatus is to be wirelessly connected, and it becomes possible to provide a suitable operational feel for the operator.

Note that the above explanation described an example using the infrastructure mode of wireless LAN as the wireless communication specification. However, the first embodiment can also be implemented by the ad hoc mode of wireless LAN or another wireless communication specification (Bluetooth® or the like).

(First Modification)

Processing of a case in which wireless communication cannot be established with the X-ray imaging apparatus by using the connection setting information associated with the selected imaging condition will be described below as the first modification.

<System Arrangement>

Figure 3:
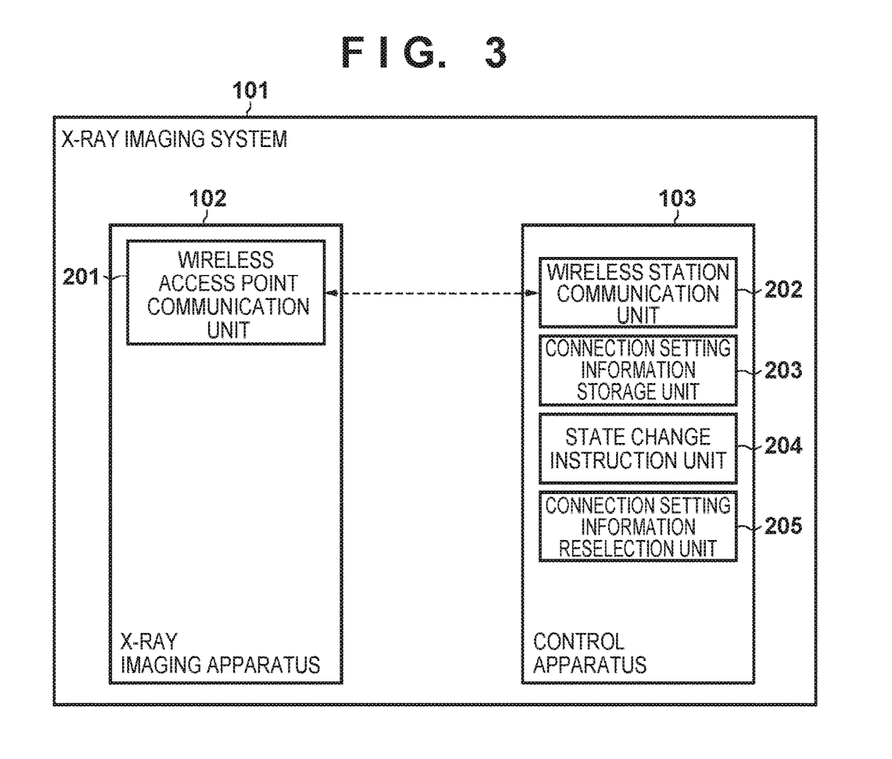
FIG. 3 is a view showing the arrangement of the X-ray imaging system according to the first modification.

FIG. 3 is a view showing the arrangement of the X-ray imaging system according to the first modification. The X-ray imaging system differs from that of the first embodiment in that the control apparatus 103 further includes a state change instruction unit 204 and a connection setting information reselection unit 205. The state change instruction unit 204 is a functional unit that instructs the X-ray imaging unit 102 to shift to an imaging enabled state. The connection setting information reselection unit 205 is a functional unit that reselects the connection setting information. A more specific description of the operation will be given below.

Figure 4:
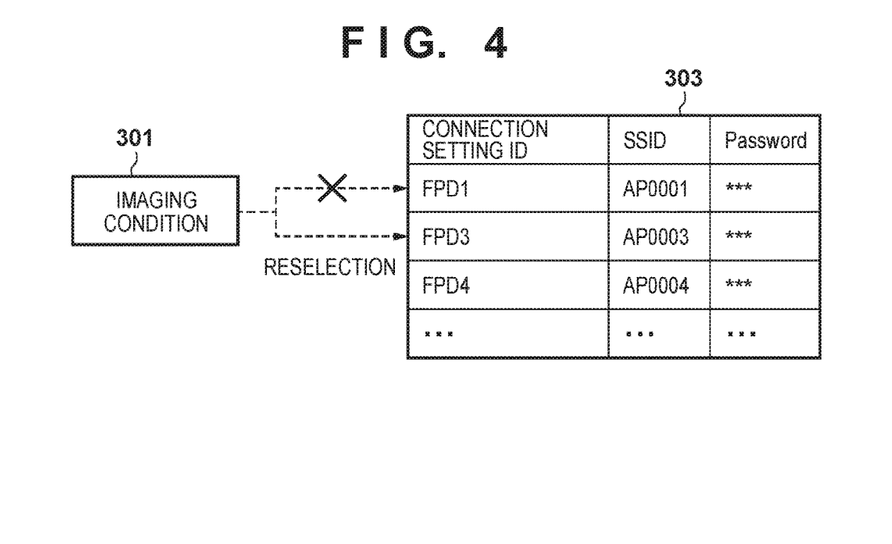
FIG. 4 is a view for explaining the reselection of connection setting information according to the first modification.

FIG. 4 is a view for explaining association of the imaging condition and the connection setting information and reselection of the connection setting information according to the first modification. As shown in FIG. 4, in the first modification, a connection setting information table 303 including two or more pieces of setting information is associated in advance with an imaging condition 301.

<System Operation>

Figure 5:
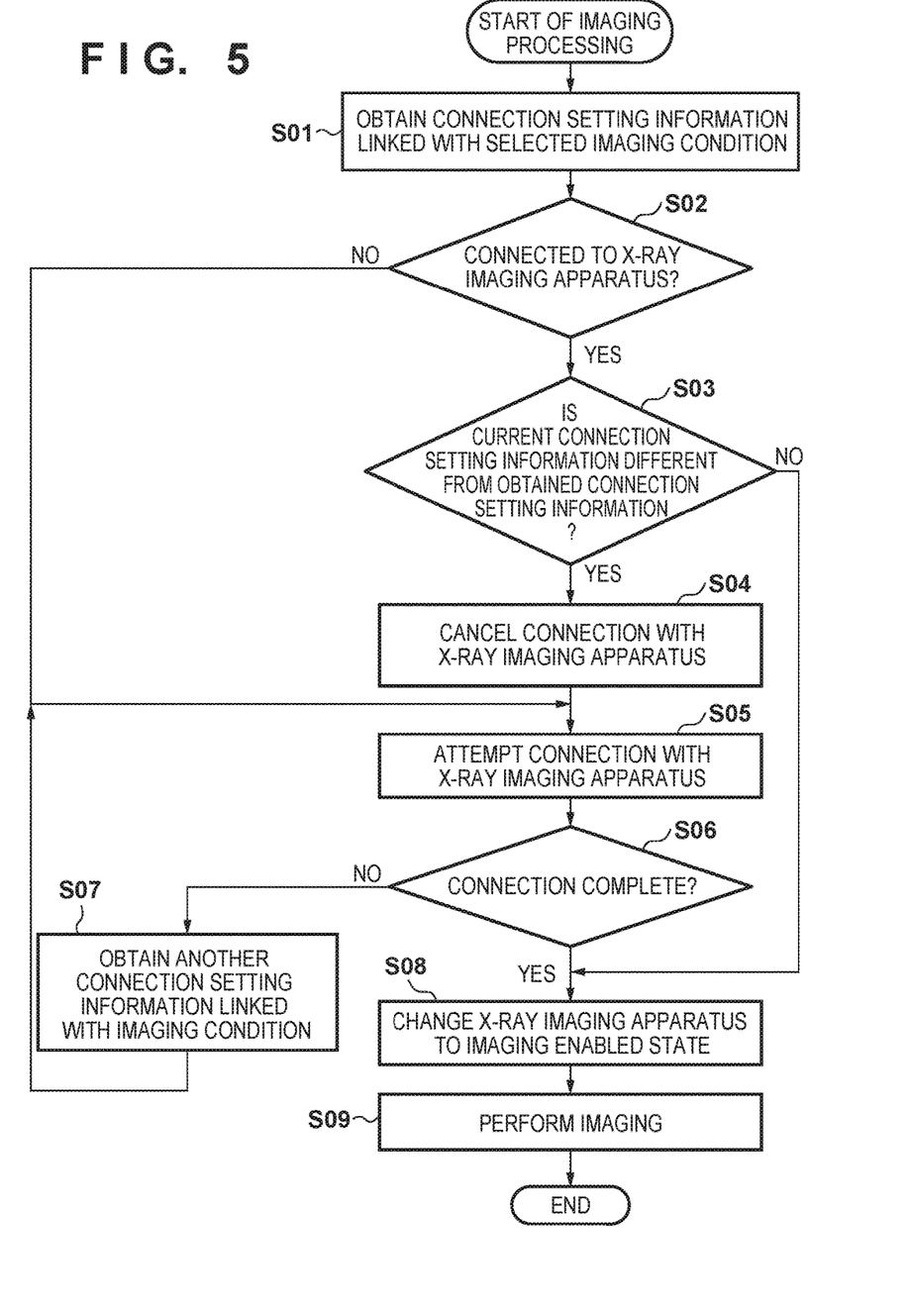
FIG. 5 is a flowchart of processing according to the first modification.

FIG. 5 is a flowchart of the processing according to the first modification. More specifically, it shows the processing sequence for selecting (reselecting) the connection setting information in a case in which connection could not be established with a predetermined X-ray imaging apparatus. The following sequence starts when the control apparatus 103 accepts the imaging condition selected by the operator. Note that the processing can be configured so that the control apparatus 103 will automatically select the imaging condition based on imaging reservation information set in advance.

In step S01, the control apparatus 103 refers to the connection setting information storage unit 203 and obtains one piece of connection setting information from the connection setting information table 303 linked with the imaging condition 301.

In step S02, the control apparatus 103 checks whether it is connected to one of the X-ray imaging apparatuses. If the control apparatus 103 is connected to one of the X-ray imaging apparatuses, the process advances to step S03. Otherwise, the process advances to step S05.

In step S03, the control apparatus 103 determines whether the connection setting information which is being used to connect with the X-ray imaging apparatus matches with the connection setting information obtained in step S01. If the connection setting information is different, the process advances to step S04. If the connection setting information matches, the process advances to step S08. In step S04, the control apparatus 103 cancels the connection with the currently connected X-ray imaging apparatus. Note that if the connection is to be canceled, the state change instruction unit 204 can also be configured to instruct the currently connected X-ray imaging apparatus 102 to shift from the imaging enabled state to a standby state (sleep state) before the cancellation. In step S05, the control apparatus 103 connects with another X-ray imaging apparatus based on the connection setting information obtained in step S01.

In step S06, the control apparatus 103 determines whether a connection with the X-ray imaging apparatus has been established in step S05. If the connection has been established, the process advances to step S08. Otherwise, the process advances to step S07. In step S07, the control apparatus 103 refers to the connection setting information storage unit 203 and obtains one piece of connection setting information from the connection setting information table 303 linked with the imaging condition 301. The control apparatus 103, however, performs control to obtain connection setting information other than the connection setting information (connection setting information that could not establish connection with the X-ray imaging apparatus in step S05) obtained in step S01. Subsequently, the process advances to step S05, and the control apparatus 103 performs again the connection processing with the X-ray imaging apparatus by using the newly selected connection setting information. Note that, in step S07, if another connection setting information could not be obtained (if connection has failed for all the connection setting information in the connection setting information table 303), it is determined that automatic selection has failed.

In step S08, the state change instruction unit 204 of the control apparatus 103 instructs the connected X-ray imaging apparatus 102 to shift to the imaging enabled state.

In step S09, the control apparatus 103 executes X-ray imaging by controlling the X-ray imaging apparatus 102 via the established wireless connection.

(Second Modification)

Processing of selecting (reselecting) connection setting information in a situation where there is imaging reservation information related to a succeeding imaging will be described below as the second modification. Note that the system arrangement is the same as that in the first modification and a description thereof will be omitted.

<System Operation>

Figure 6:
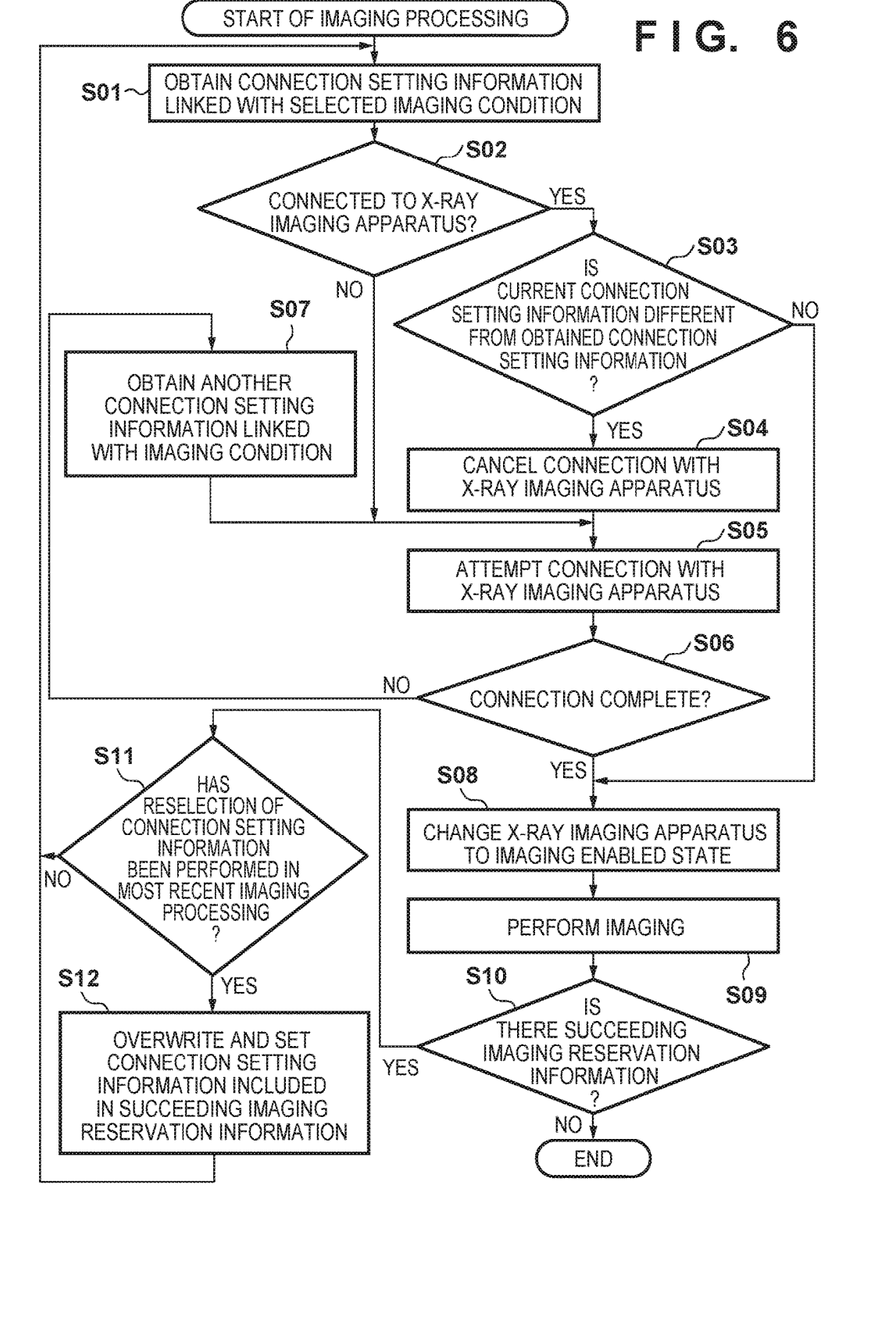
FIG. 6 is a flowchart of processing according to the second modification.

FIG. 6 is a flowchart of the processing according to the second modification. More specifically, it shows the processing sequence of selecting the connection setting information in a situation where there is imaging reservation information related to the succeeding imaging. Note that the processes of steps S01 to S09 are the same as those in the above-described first modification and a description thereof will be omitted. Note that the imaging reservation information includes the connection setting information.

When imaging is completed in step S09, the control apparatus 103 determines whether there is imaging reservation information related to a succeeding imaging in step S10. If there is imaging reservation information, the process advances to step S11. Otherwise, the processing ends.

In step S11, the control apparatus 103 determines whether reselection of connection setting information (process of step S07) was performed in the immediately preceding imaging processing loop (steps S01 to 09). If reselection was performed, the process advances to step S12. Otherwise, the process advances to step S01.

In step S12, the control apparatus 103 changes the connection setting information included in the imaging reservation information. More specifically, the connection setting information from before reselection in the immediately preceding imaging processing loop (that is, connection setting information that has been confirmed to be incapable of establishing connection) is overwritten and set by the connection setting information after reselection which was set at the time of actual imaging in the immediately preceding imaging processing loop. Subsequently, the process advances to step S01.

According to the above-described processes of steps S10 to S12, unnecessary connection processing (that is, attempts to establish connection using connection setting information that has been confirmed to be incapable of establishing connection) can be omitted in the succeeding imaging.

(Third Modification)

Another processing of selecting (reselecting) connection setting information in a situation where there is imaging reservation information related to a succeeding imaging will be described below as the third modification. Note that the system arrangement is the same as those in the first and second modifications and a description thereof will be omitted.

<System Arrangement>

Figure 7:
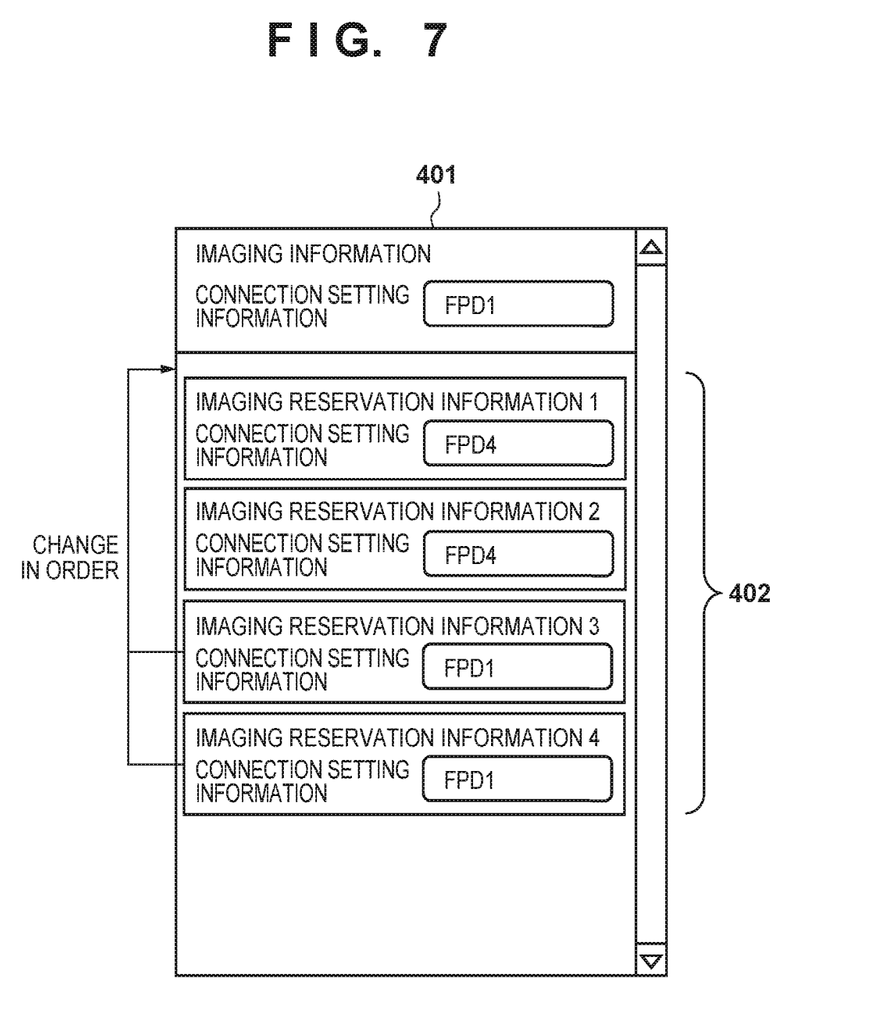
FIG. 7 is a view for explaining imaging reservation order change according to the third modification.

FIG. 7 is a view for explaining imaging reservation order change according to the third modification. In FIG. 7, an imaging reservation that is registered closer to the top of the list has a stronger correspondence with the preceding imaging operation.

More specifically, imaging information 401 represents information of imaging that is currently in progress, and imaging reservation information 402 represents imaging information of imaging which is currently on standby. In this case, assume that imaging processing will be performed in order from the imaging information positioned on the upper portion of the list of the imaging reservation information 402.

Assume that the imaging information 401 being used in the current imaging operation (most recent imaging) includes connection setting information 302 having "FPD1" as the connection setting information index. Assume also that four pieces of imaging reservation information 1 to 4, as shown in FIG. 7, are included as the imaging reservation information 402.

In this case, the control apparatus 103 is currently connected to an access point (X-ray imaging apparatus) which has "FPD1" as the index, it will need to return to the connection with "FPD1" after switching to "FPD4" in the succeeding imaging. That is, wireless connection switching will occur twice, and the time until completion of the imaging will be long.

Therefore, in the third modification, control is performed to execute ahead the imaging of the imaging reservation information that has the same connection setting information as the currently used connection setting information ("FPD1"). More specifically, the order of imaging operations that succeed the imaging information 401 is changed from imaging reservation information 1→imaging reservation information 2→imaging reservation information 3→imaging reservation information 4 to imaging reservation information 3→imaging reservation information 4→imaging reservation information 1→imaging reservation information 2.

From this control, the wireless connection switching count until the completion of imaging can be reduced to one, and it becomes possible to shorten the time till the completion of imaging.

Second Embodiment

The second embodiment of an imaging system according to the present invention will be described below by taking an X-ray imaging system using both wired and wireless LANs as an example.

<System Arrangement>

Figure 8:
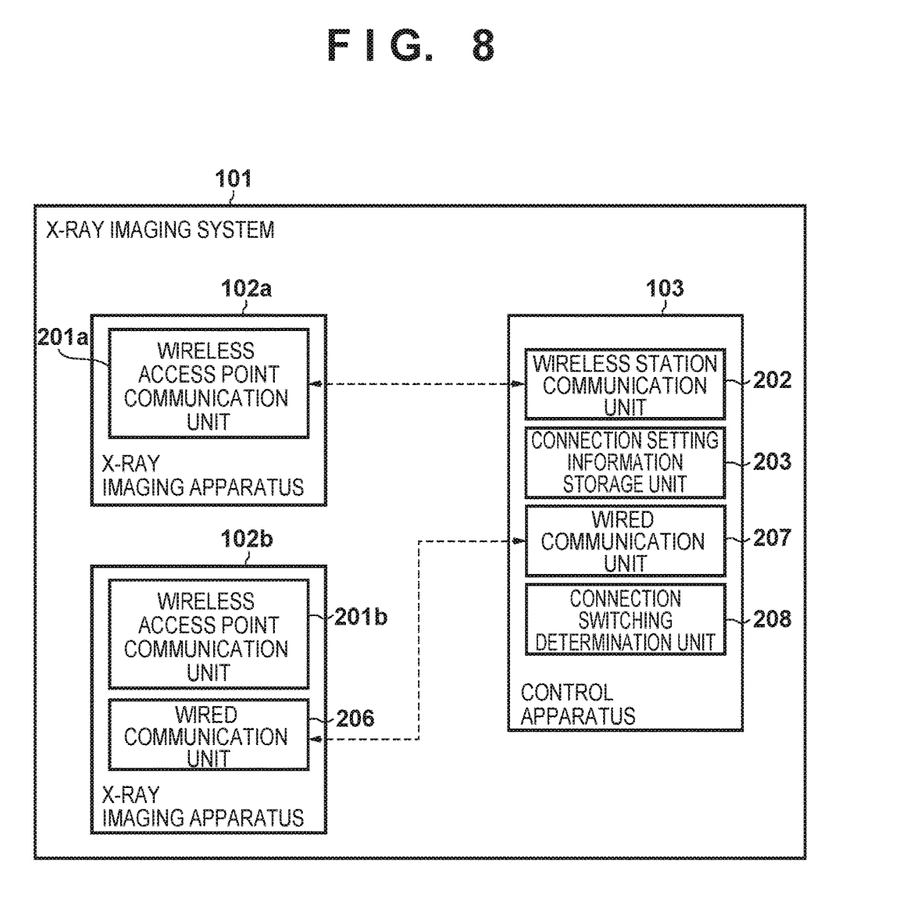
FIG. 8 is a view showing the arrangement of an X-ray imaging system according to the second embodiment.

FIG. 8 is a view showing the arrangement of an X-ray imaging system according to the second embodiment. The X-ray imaging system is, for example, installed in a visiting car (a mobile X-ray apparatus). The X-ray imaging system differs from that of the first embodiment in that it includes an X-ray imaging apparatus 102b configured to be connectable by wireless LAN and wired LAN in addition to an X-ray imaging apparatus 102a which is connectable by wireless LAN only. Note that the X-ray imaging apparatus 102b has been formed to perform wired communication if communication by wired LAN has been established and be capable of establishing communication via wireless LAN if communication by wired LAN is disconnected.

In addition, a control apparatus 103 further includes a wired communication unit 207 and a connection switching determination unit 208. The wired communication unit 207 is a functional unit for communicating with the X-ray imaging apparatus 102b via the wired LAN. The connection switching determination unit 208 is a functional unit that determines which X-ray imaging apparatus is to be connected and whether to connect by wired or wireless LAN.

<System Operation>

In the initial state, assume that the control apparatus 103 is connected with the X-ray imaging apparatus 102a via a wireless station communication unit 202. Assume also that the control apparatus 103 is also connected to the X-ray imaging apparatus 102b via a wired connection unit 206.

In a case in which the wired connection with the X-ray imaging apparatus 102b is canceled, that is, if connection by wired communication is impossible, the connection switching determination unit 208 determines, based on the currently selected imaging condition, the priority of the X-ray imaging apparatus to be connected. For example, if an imaging condition that uses the X-ray imaging apparatus 102a is currently selected, the connection switching determination unit 208 determines that the priority of the X-ray imaging apparatus 102a is higher and continues to maintain the wireless connection with the X-ray imaging apparatus 102a. On the other hand, if an imaging condition that uses the X-ray imaging apparatus 102b is selected, the connection switching determination unit 208 determines that the priority of the X-ray imaging apparatus 102b is higher. In this case, the connection switching determination unit 208 gives instructions to cancel the wireless connection with the X-ray imaging apparatus 102a and to newly establish a wireless connection with the X-ray imaging apparatus 102b.

According to the above-described operation, even if the wired connection is canceled, it is possible to continue communication with the suitable X-ray imaging apparatus.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-073214, filed Mar. 31, 2015 which is hereby incorporated by reference herein in its entirety.

What is claimed is:

1. An imaging system comprising an image capturing apparatus and a control apparatus that selectively performs wireless connection with the image capturing apparatus,
wherein the image capturing apparatus comprises a wireless access point communication unit configured to operate as a unique wireless access point device, and
the control apparatus comprises
a wireless station communication unit configured to operate as a wireless station device,
a storage unit including a memory to store, in association with a predetermined imaging condition, connection setting information for wirelessly connecting with the image capturing apparatus, and
a connection control unit including a memory storing instructions and a processor to execute the instructions to set, if an imaging condition designated by a user matches with the predetermined imaging condition, the connection setting information associated with the predetermined imaging condition in the wireless station communication unit and perform control so as to wirelessly connect with the image capturing apparatus.

2. The system according to claim 1, wherein the predetermined imaging condition includes one of a unique identifier of image capturing apparatus, a type of image capturing apparatus, a body part to be imaged, and an imaging direction.

3. The system according to claim 1, wherein the imaging system includes a plurality of image capturing apparatuses, wherein
the memory in the storage unit stores, in association with the predetermined imaging condition, at least two pieces of connection setting information for wirelessly connecting with at least two image capturing apparatuses, respectively, out of the plurality of image capturing apparatuses, and
the processor in the connection control selects, if an imaging condition designated by the user matches with the predetermined imaging condition, one piece of connection setting information out of the at least two pieces of connection setting information associated with the predetermined imaging condition and sets the selected connection setting information in the wireless station communication unit, and selects, if wireless connection with the image capturing apparatus by the one piece of connection setting information fails, another piece of connection setting information out of the at least two connection setting information and sets the selected connection setting information in the wireless station communication unit.

4. The system according to claim 3, wherein the processor in the connection control unit instructs a wirelessly connected image capturing apparatus to shift to an imaging enabled state.

5. The system according to claim 3, wherein the processor connection control unit changes, if there is imaging reservation information designating succeeding imaging and a selection of connection setting information in most recent imaging, connection setting information obtained before selection and included in the imaging reservation information to connection setting information obtained after the selection.

6. The imaging system according to claim 1, wherein the processor in the connection control unit executes, if there is a plurality of pieces of imaging reservation information designating succeeding imaging and both first imaging reservation information using connection setting information which is same as connection setting information used in most recent imaging and second imaging reservation information using connection setting information which is different from the connection setting information used in the most recent imaging are included in the plurality of pieces of imaging reservation information, imaging by the first imaging reservation information before imaging by the second imaging reservation information.

7. An imaging system comprising a first image capturing apparatus, a second image capturing apparatus, and a control apparatus configured to selectively connect with one of the first and second image capturing apparatuses,
   wherein the first image capturing apparatus comprises
   a first wireless access point communication unit configured to operate as a first wireless access point device,
   the second image capturing apparatus comprises
   a second wireless access point communication unit configured to operate as a second wireless access point device, and
   a first wired communication unit configured to perform wired communication with the control apparatus,
   the control apparatus comprises
   a wireless station communication unit configured to operate as a wireless station device,
   a second wired communication unit configured to perform wired communication with the second image capturing apparatus,
   a storage unit including a memory to store, in association with a predetermined imaging condition, connection setting information for connecting to one of the first image capturing apparatus and the second image capturing apparatus, and
   a connection control unit including a memory storing instructions and a processor to execute the instructions to set, if an imaging condition designated by a user matches with the predetermined imaging condition, the connection setting information associated with the predetermined imaging condition in the wireless station communication unit and performs control so as to connect with one of the first and second image capturing apparatuses, and
   if connecting to the second image capturing apparatus, the connection control unit connects by wired connection if wired connection via the second wired communication unit is possible and connects by wireless communication via the wireless station communication unit if the wired connection via the second wired communication unit is impossible.

8. A control apparatus that selectively and wirelessly connects with an image capturing apparatus operating as a unique wireless access point device, comprising:
   a wireless station communication unit configured to operate as a wireless station device,
   a storage unit including a memory to store, in association with a predetermined imaging condition, connection setting information for wirelessly connecting with the image capturing apparatus, and
   a connection control unit including a memory storing instructions and a processor to execute the instructions to set, if an imaging condition designated by a user matches with the predetermined imaging condition, the connection setting information associated with the predetermined imaging condition in the wireless station communication unit and perform control so as to wirelessly connect with the image capturing apparatus.

9. A control method of a control apparatus that selectively and wirelessly connects with an image capturing apparatus operating as a unique wireless access point device,
   wherein the control apparatus comprises a storage unit including a memory to store, in association with a predetermined imaging condition, connection setting information for wirelessly connecting with the image capturing apparatus, and
   the control method comprises the steps of:
   accepting designation of an imaging condition from a user, and
   performing connection control so as to wirelessly connect to the image capturing apparatus by using the connection setting information associated with the predetermined imaging condition if the imaging condition accepted in the accepting matches the predetermined imaging condition.

10. A non-transitory computer-readable recording medium storing a program that causes a computer to function as a control apparatus that selectively and wirelessly connects with an image capturing apparatus operating as a unique wireless access point device, the program causing the computer to:
    operate a wireless station communication unit as a wireless station device,
    store, in association with a predetermined imaging condition, connection setting information for wirelessly connecting with the image capturing apparatus, and
    set, if an imaging condition designated by a user matches with the predetermined imaging condition, the connection setting information associated with the predetermined imaging condition in the wireless station communication unit and perform control so as to wirelessly connect with the image capturing apparatus.

* * * * *